United States Patent [19]

Fukuto et al.

[11] Patent Number: 5,064,820

[45] Date of Patent: Nov. 12, 1991

[54] ALKYL SUBSTITUTED PHOSPHATES AND PHOSPHONATES AS DISRUPTANTS OF INSECT SEX PHEROMONE-MEDIATED BEHAVIOR

[75] Inventors: T. Roy Fukuto; Richard S. Vetter; Thomas C. Baker; Mangel S. Malik, all of Riverside, Calif.

[73] Assignee: Regents of the University of California, Alameda, Calif.

[21] Appl. No.: 452,645

[22] Filed: Dec. 19, 1989

[51] Int. Cl.$^5$ .......................... A01N 57/34; C07F 9/42
[52] U.S. Cl. ..................... 514/134; 558/201; 558/202
[58] Field of Search ............... 558/201, 202; 514/134

[56] References Cited

U.S. PATENT DOCUMENTS 4,924,024  5/1990  Biller .................... 558/202

FOREIGN PATENT DOCUMENTS 70382  3/1987  Japan .................... 558/201

OTHER PUBLICATIONS

Baker, T. C., Experientia, 45, 248–262, (1989).

Thompson, C. M. et al., J. Org. Chem., 49, 1969–99, (1984).

Primary Examiner—Nicholas S. Rizzo
Assistant Examiner—E. Bernhardt
Attorney, Agent, or Firm—Nilsson, Robbins, Dalgarn, Berliner, Carson & Wurst

[57] ABSTRACT

Compounds of the general formula I

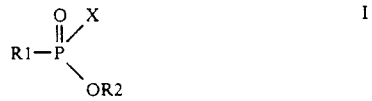

wherein
R1 represents —R3, —OR3 or —N(R3)$_2$, in which R3 is alkyl of 1 to about 18 carbon atoms;
R2 represents alkyl of 1 to about 18 carbon atoms; and
X represents —OR3, halogen, —CN, —SR4 or —N(R4)$_2$, in which R4 is alkyl of 1 to about 5 carbon atoms, which the proviso that at least one of R2 and R3 is a pheromone alkyl chain. Members of this class of compounds have been shown to exhibit outstanding activity in disrupting pheromone-mediated behavior of various insects, in particular moths.

16 Claims, No Drawings

ALKYL SUBSTITUTED PHOSPHATES AND PHOSPHONATES AS DISRUPTANTS OF INSECT SEX PHEROMONE-MEDIATED BEHAVIOR

BACKGROUND OF THE INVENTION

This invention relates to compositions and methods for disruption of insect behaviors mediated by sex pheromones.

A number of attempts are being made to find new biorational and environmentally safe methods for insect pest control. Particular interest has been focused in the field of insect pheromones and other semiochemicals (i.e., chemicals which function as a signal to the organism).

An adult male moth is able to locate a pheromone-emitting female or synthetic pheromone source by a program of in-flight upwind steering (optomotor anemotaxis) and a program of counterturning. Both programs are switched on by the correct species-specific pheromone blend, and thus successful orientation and mating depends on initial olfactory events that occur at the antennal level. The crucial events involved in pheromone olfaction include adsorption of the airborne pheromone onto the antennal surface, followed by diffusion to a receptor site with subsequent binding and activation of the receptor, either by directly opening ion channels in the membrane or by activating a second messenger in order to cause a change in membrane conductance.

Recent evidence indicates that the intermittency of the pheromone signal in a natural plume that has a fine, filamentous structure is required in order for the insect to exhibit the sustained upwind flight that is necessary for location of the pheromone source. Further evidence at the single antennal neuron level indicates that the inability of the antenna to rapidly inactivate the pheromone molecules before the next filament arrives (usually in one second or less) contributes to adaptation of the neurons, which is also correlated with the cessation of sustained upwind flight.

Inactivation is believed to involve, among other things, the chemical alteration of the pheromone to an inactive form. In those cases where the pheromone is a carboxylic ester, chemical alteration is achieved by rapid hydrolytic degradation mediated by a carboxylesterase to the inactive alcohol and acid [Ferkovich et al., J. Chem. Ecol. 8:859-66 (1982)].

Among the approaches to the understanding of the molecular mechanism of pheromones activating the transductory process in insect neurons currently being investigated are (i) the use of radioligands to characterize the pheromone binding sites, and (ii) synthesis and determination of relative activities of pheromone analogs. With respect to the latter approach, the analogs Z9-14:Nmc [A], Z9-14:Tfa [B], Z9-14:Tca [C] and (Z)-12-heptadecen-2-one [D] have been reported to show reversible inhibition of electrophysiological and behavioral responses in *Heliothis virescens* [Baker et al., European Patent Appln. 42228 (1981); Albans et al., Crop Prot. 3:501-06 (1984)].

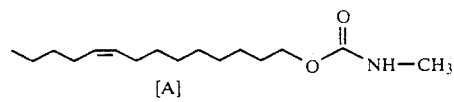
[A]

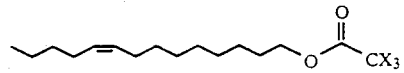
[B], X = F
[C], X = Cl

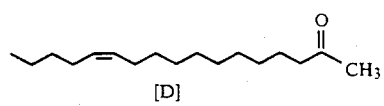
[D]

Recently, mono-, di- and tri-halogenated acetates [E], diazoacetate [F] and trifluoromethyl ketone [G] analogs of Z11-16:Ac, pheromone of *Plutella xylostella*, were studied as competitive inhibitors of antennal esterases [Prestwich and Streinz, J. Chem. Ecol. 14: 1003-21 (1988)]. The fluoro compounds showed greater inhibition of esterases, but were electrophysiologically less active than the natural pheromone. The compounds were not investigated further. No disruption of behavioral orientation to the natural pheromone blend was demonstrated for these compounds.

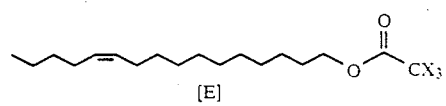
[E]

X = H, Cl, Br, I (mono, di or tri)

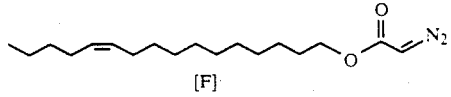
[F]

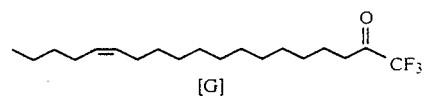
[G]

It is an object of the present invention to provide novel compositions which interfere with the orientation and mating of a wide range of insect species.

It is a particular object of the present invention to provide compositions and methods useful to disrupt insect mating by selective inhibition of the antennal carboxylesterase enzyme.

It is a further object of the present invention to provide such compositions and methods which have a high species specificity and reduced toxicity to other organisms relative to other insecticides heretofore in general use.

SUMMARY OF THE INVENTION

The present invention is based on the premise that insect antennal pheromone carboxylesterase is inhibited by at least one compound selected from a novel class of organophosphorous esters. In particular, the present invention is directed to compounds of the general formula I

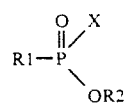

wherein

R1 represents —R3, —OR3 or —N(R3)₂, in which R3 is alkyl of 1 to about 18 carbon atoms;

R2 represents alkyl of 1 to about 18 carbon atoms; and

X represents —OR3, halogen, —CN, —SR4 or —N(R4)2, in which R4 is alkyl of 1 to about 5 carbon atoms,
with the proviso that at least one of R2 and R3 is a pheromone alkyl chain.

Members of this class of compounds have been shown to exhibit outstanding activity in disrupting pheromone-mediated behavior of insects, in particular moths.

DETAILED DESCRIPTION OF THE INVENTION

The compounds of the invention are designed to provide a novel and safe means of controlling insects by disrupting their mating. This desirable result should be achieved not through central nervous system habituation or by misdirecting males as do natural pheromone components, but by causing adaptation of the antennal sensory neurons.

Inhibition of the carboxylesterase enzyme, presumably by phosphorylation of the enzyme by the organophosphorous ester, should result in an accumulation of the pheromone at the receptor sites, leading to saturation of the sites and adaptation of the antennal neurons. The inability of the cells to disadapt and fire with subsequent exposure to newly-arriving pheromone turns off both of the programs involved in upwind flight orientation, and thus prevents males from locating females for mating.

Specific members of this class of compounds are useful in controlling insects which utilize esters (in particular, acetate esters) as major or minor components of the female's sex pheromone communication blends, as a consequence of the corresponding compounds' effects on antennal pheromone esterases. Thus, for any given insect species one or more compounds according to general formula I wherein the pheromone alkyl chain corresponds to the pheromone alkyl skeleton of an ester comprising the sex pheromone blend of that particular species will be particularly suited for inhibition of the insect's antennal esterase. It is therefore possible to develop a specific composition for use in controlling the population of a particular insect species whose sex pheromone blend includes at least one ester by preparing one or more compounds of general formula I with at least one corresponding pheromone alkyl group. It is believed that the presence in a compound of general formula I of at least one such corresponding pheromone alkyl group is important for achieving specific inhibition of the antennal esterase of a particular species.

As is well known to those of skill in the art, the sex pheromone blends of a wide variety of insects contain one or more ester components, in particular acetates. Because the antennal esterase is believed to be involved in the orientation behavior whenever one or more such esters is a component of the sex pheromone blend, the present invention is of general applicability to a substantial number of different insect species. By way of illustration, the following families have been reported to include at least one species which should be amenable to control through the use of a corresponding compound of general formula I, in view of the presence in the pheromone blend of the species of at least one ester component: Tineidae, Hieroxestidae, Gracillariidae, Ethmiidae, Oecophoridae, Xyloryctidae, Coleophoridae, Cosmopterigidae, Gelechiidae, Glyphipterigidae, Yponomeutidae, Plutellidae, Argyresthiidae, Stathmopodidae, Acrolepiidae, Sesiidae, Tortricidae, Cossidae, Lasiocampidae, Attacidae, Sphingidae, Zygaenidae, Pterophoridae, Thyrididae, Pyralidae, Drepanidae, Geometridae, Epiplemidae, Thaumetopoeidae, and Noctuidae. Exemplary insects known to employ such sex pheromone communication blends containing esters include Grapholita sp., Trichoplusia sp., Argyrotaenia sp., Archips sp., Phyllonorycter sp., Coleophora sp., Pectinophora sp., Synanthedon sp., Choristoneura sp., Adoxophyes sp., Platinota sp., Pandemis sp., Lobesia sp., Eucosma sp., Rhyacionia sp., Cydia sp., Plutella sp., Spodoptera sp., Agrotis sp., and Ostrinia sp. The present invention is broadly applicable with respect to the large number of species for which the composition of the pheromone sex blend has already been reported to include at least one ester component, as well as to species hereinafter determined to utilize such ester-containing pheromone blends. In addition to the large number of individual reports, various lists of sex pheromone compositions have been published, to which reference may be made for an illustration of the substantial variety of species which should be amenable to control in accordance with the present invention. One such list, hereby incorporated by reference, is Arn et al., "List of sex pheromones of lepidoptera and related attractants," OILB-SROB/IOBC-WPRS (Paris, France 1986).

Of particular interest are a class of esters of the general formulas II and III

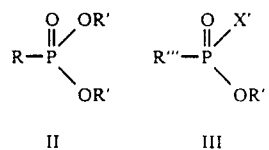

wherein R represents alkyl or alkoxy of 1 to about 5 carbon atoms; R' represents a pheromone alkyl chain; X' represents halogen, —CN, —SR" or —N(R")2, in which R" is alkyl of 1 to about 5 carbon atoms; and R''' represents alkyl or alkoxy wherein the alkyl moiety is a pheromone alkyl chain. Most preferred are the phosphorohalidate and phosphonohalidate esters of Formula III wherein X' is halogen, especially fluorine.

By "pheromone alkyl chain" is meant the characteristic alkyl backbone found in the naturally-occurring pheromones, and in particular, those pheromones which are present as major or minor components of sex pheromone mixtures in the form of esters. A larger number of such pheromone alkyl chains have already been identified and are well known by workers in the field. Exemplary pheromone alkyl chains include: cis—CH3—(CH2)5—CH=CH—(CH2)2—; cis—CH3—(CH2)3—CH=CH—(CH2)4—; cis—CH3—(CH2)3—CH=CH—(CH2)6—; cis—CH3—(CH2)2—CH=CH—(CH2)7—; trans—CH3—(CH2)3—CH=CH—(CH2)6—; cis—CH3—(CH2)5—CH=CH—(CH2)4—; trans—CH3—(CH2)5—CH=CH—(CH2)4—; trans—CH3—(CH2)2—CH=CH—(CH2)7—; trans—CH3—CH=CH—(CH2)9—; cis—CH3—CH2—CH=CH—(CH2)8—; trans—CH3—CH2—CH=CH—(CH2)8—; trans-8, trans-10-CH3—CH=CH—CH=CH—(CH2)7—; cis—CH3—(CH2)7—CH=CH—(CH2)3—; cis-4, trans-7-CH3—(CH2)4—CH=CH—CH2—CH=CH—(CH2)3—; cis—CH3—(CH2)2—CH=CH—(CH2)9—; trans—CH3—(CH2)4—CH=CH—(CH2)7—; cis—CH3—CH2—CH=CH—(CH2)-

10—; trans-CH$_3$—CH$_2$—CH=CH—(CH$_2$)$_{10}$—; cis—CH$_3$—(CH$_2$)$_5$—CH=CH—(CH$_2$)$_6$—; cis—CH$_3$—(CH$_2$)$_3$—CH=CH—(CH$_2$)$_8$—; cis-9, trans-12-CH$_3$—CH=CH—CH$_2$—CH=CH—(CH$_2$)$_8$—; cis-9, trans-11-CH$_3$—CH$_2$—CH=CH—CH=CH—(CH$_2$)$_8$—; cis—CH$_3$—(CH$_2$)$_3$—CH=CH—(CH$_2$)$_{10}$—; cis—CH$_3$—(CH$_2$)$_5$—CH=CH—(CH$_2$)$_8$—; cis-7, cis-11-CH$_3$—(CH$_2$)$_3$—CH=CH—(CH$_2$)$_2$—CH=CH—(CH$_2$)$_6$—; cis-7, trans-11-CH$_3$—(CH$_2$)$_3$—CH=CH—(CH$_2$)$_2$—CH=CH—(CH$_2$)$_6$—; and cis-3, cis-13—CH$_3$—(CH$_2$)$_3$—CH=CH—(CH$_2$)$_8$—CH=CH—(CH$_2$)$_2$—.

The compounds of the invention may be used individually, in mixtures of two or more such compounds, or in admixture with one or more naturally-occurring pheromones. Administration of the compounds is generally effected in the same manner as conventionally employed in connection with the use of naturally-occurring pheromones and analogues, or mixtures thereof. Such methods for the use of the naturally-occurring pheromones in pest control are well known to those working in the art. Generally, it is desirable to administer the compounds in some type of controlled release form, to prevent rapid evaporation of the compounds. For example, the compounds may be employed in some type of controlled-release matrix. Suitable modes of administration include microencapsulated beads, hollow fibers, porous tubes or laminated flakes. Various types of controlled-release dispensers are also well known to those of skill in the art, and may suitably be employed in accordance with the present invention.

Similarly, the rate of application of the compounds of the invention may be varied over a fairly broad range, as is the case with respect to the naturally-occurring compounds or analogues thereof. In general, application rates of about 0.1 gram to about 1000 grams, preferably about 1 to about 100 grams, per acre are employed. In some instances, it may be advantageous to employ a limited number of highly-concentrated sources of the compounds, individually or in admixture with the naturally-occurring compounds; alternatively, a larger number of smaller point sources may be more appropriate for use in a given environment. In view of the presumed mechanism of action of the compounds of the invention, it may also be particularly advantageous to dispense one or more compounds of the invention from one dispenser while simultaneously dispensing a natural pheromone or pheromone mixture from a separate dispenser; in this manner, an effective enhancement of the field life of the natural pheromone or pheromone mixture would be achieved.

Various alkyl substituted phosphates and phosphonates were synthesized and tested for disruption of behaviour in the oriental fruit moth (*Grapholita molesta*). Some of the compounds incorporating a pheromone alkyl chain were found to exhibit remarkable activity. Further, these were either non toxic or much less toxic to house flies and mammals than conventional organophosphorous insecticides.

When males were pre-exposed to some of the fluorophosphate esters, the number of moths subsequently responding to a plume of the natural pheromone blend by flying upwind and locating the source dropped to nearly zero, which is very similar to the effect of pre-exposure to the major sex pheromone component (Z)-8-dodecenyl acetate. It is known that pre-exposure to large quantities of natural pheromone causes male moths to become chemosensorily habituated and thus unable to detect and respond to sex pheromone present in the air. Exposure of the males to some of the fluorophosphate esters also elicited wing-fanning behavior similar to that caused by the natural sex pheromone. Wing fanning is normally a pheromone-mediated response that occurs both before take-off and upwind flight, as well as during courtship after landing near a female.

Several compounds of the present invention caused both wing fanning during pre-exposure and disruption (prevention) of upwind flight during subsequent exposure of males to a plume of the natural pheromone blend. This activity profile is similar to that observed with the major pheromone component (Z)-8-dodecenyl acetate. It is believed, however, that the mechanism of action of the compounds of the present invention is different from that of the natural pheromone components, because wind tunnel experiments with several compounds of the invention revealed no upwind flight of moths in the same manner observed for the pheromone blend.

The invention will be better understood by reference to the following example which is intended for purposes of illustration and is not to be construed as in any way limiting the scope of the present invention, which is defined in the claims appended hereto.

EXAMPLE

Synthesis of various experimental compounds of the general formulas II and III was performed as follows. The starting compounds of general formula IV

wherein R is as previously defined were either prepared by literature methods (for example, from the corresponding compound wherein R is Cl) or purchased from Aldrich Chemical Company, Milwaukee, Wis. and were reacted with the appropriate alcohol R'—OH in the presence of pyridine at 0°–5° C. in benzene as a solvent. Pyridine hydrochloride formed in the reaction was filtered out and the crude chloridates of general formula V

were obtained in good yield. The disubstituted compounds of general formula II were either formed as minor products during the formation of the compounds of general formula V, or synthesized directly using two moles of alcohol to react with one mole of the compound of general formula IV. Refluxing of chloridates of general formula V in benzene with anhydrous potassium fluoride, potassium cyanide, or secondary amine under vigorous stirring and stirring of the compound wherein R is OEt with the sodium salt of ethanethiol in ether resulted in the corresponding compounds of general formula III. The crude products were purified by flash chromatography over silica 32-63 (40 micron) using hexane:ethyl acetate (1:1) as the solvent system. Spectral and analytical data of the compounds are given in Tables 1 and 2, wherein the compounds of general formula V are designated as 2a-2j; the compounds of general formula II are designated as 3a-3c; and the compounds of general formula III are designated as 4a-4m. In general formula III, X' is F in compounds 4a-4j, CN in compound 4k, SEt in compound 4l and NEt$_2$ in compound 4m.

The examination of the housefly toxicity of the compounds showed nontoxic to weak toxicity. Selected compounds were tested for mammalian toxicity against Swiss white mice (Swiss Webster) at 100 mg/kg of the body weight. None of the compounds were found toxic at this dose. Compound 4j was tested at 300 mg/kg and no toxic effects were observed.

The behavioral bioassay was performed against 3- to 5-day-old oriental fruit moths (*Grapholita molesta*). Dilutions were made of each compound. The compounds were then loaded onto filter paper to 1000, 100 and 10 μg, and the samples air-dried in a hood for 5 min. The impregnated paper was placed in a 1-liter foil-covered beaker containing approximately 25 male *Grapholita molesta* moths. Moths were 3-5 days old and were tested during their daily period of greatest pheromone sensitivity (the two-hour period surrounding dusk). After 5 min exposure to the compound, moths were transferred to a wind tunnel and individually placed (ten moths for each load for each compound) into a screen cone situated in a plume of sex pheromone. The pheromone source (10 μg Z-8-dodecenyl acetate with 6% E-8-dodecenyl acetate and 3% Z-8-dodecenyl alcohol) was loaded onto a rubber septum and placed at the upwind end of the tunnel. The 0.5 m/sec air speed carried the odor along the length of the tunnel across the screen cage. Control moths responded with immediate wing fanning and took flight within 10 sec; 50-80% of those released flew upwind to locate the source (Table 3). Moths exposed to most of the analogs exhibited similar percentages for source location, particularly to the saturated compounds (4b, 4c, 4f, 4h), demonstrating no deleterious effect of the fluoro-analog on the moths' ability to locate chemosensory sources. However, two of the analogs (4d, 4j) significantly inhibited the ability of the moths to locate the pheromone when compared to controls (Table 3). This is similar to the effect that the sex pheromone component, Z-8-dodecenyl acetate, has on male chemosensory activity. This inhibition was reversible 24 hours later.

A wing fanning bioassay was constructed with a 61 cm long glass tube (77 mm ID) placed in the fume hood so that air was drawn through the tube a 0.5 m/sec. For each trial, ten males were placed individually in 75 mm long glass tubes (10 mm ID) with screen ends and placed at the downwind end of the large tube. Pheromones and analogs were impregnated at the same loads and with the same procedure mentioned above. The large tube and the chemically-laden air was drawn through the tubes containing the males. Observations on the number of moths wing fanning were made for 15 sec prior to and 15 sec after introduction of the compound into the tube's airstream. As expected, Z8-12:Ac caused a significant increase in the number of males wing fanning; compounds 4d and 4j caused similar responses (Table 3). Most of the other analogs caused no change in the males' behavior, however, compounds 4g and 4i caused significant increases in wing fanning at all three loads, even though there was no statistically significant inhibition on pheromone location in the wind tunnel using these compounds. Similar results occurred with compound 4a, but increased wing fanning was observed in response to 4a at the 100 μg load only.

One hundred micrograms of pheromone blend, consisting of 10 parts cis-8-dodecenyl acetate (Z8-12:Ac), 0.06 parts trans-8-dodecenyl acetate (E8-12:Ac) and 0.03 parts cis-8-dodecenyl alcohol (Z8-12:OH) on a rubber dispenser, resulted in 75% or greater success in upwind flight location of the pheromone blend source by *Grapholita molesta* in wind tunnel experiments in which males had been preexposed only to clean air. Substitution of Z8-12:Ac with the same amount of either 4d or 4j in the blend resulted in none of the moths finding the point source of the modified blend. A ten-fold increase in the amount of this blend, or a ten-fold increase in the amount of either 4d or 4j in the blend, also resulted in no location of the blend source by the moths.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

TABLE 1

Physical and spectroscopic data of substituted phosphates and phosphonates:

| Compd. No. | R | R' | Mcl. formula | $^1$H-NMR (ppm) | $^{31}$P-NMR (ppm) | Mass M/Z MH$^+$ |
| --- | --- | --- | --- | --- | --- | --- |
| 1 | 2 | 3 | 4 | 5 | 6 | 7 |
| 2a | OMe | (CH$_2$)$_7$—CH=CH—(CH$_2$)$_2$—CH$_3$ (cis) | C$_{12}$H$_{30}$ClO$_3$P | 0.83 (t, 3H, CH$_3$, J = 7H$_z$); 1.25 [m, 10H, (CH$_2$)$_4$ & CH$_2$—CH$_3$]; 1.64 (p, 2H, OCH$_2$—CH$_2$, J = 7H$_z$); 1.95 (m, 4H, CH$_2$—CH=CH—CH$_2$); 3.85 (d, 3H, OCH$_3$, J = 12H$_z$); 4.13 (m, 2H, OCH$_2$, J$_{H-H}$ = 7 & J$_{P-H}$ = 12H$_z$); 5.31 (m, 2H, CH=CH) | 6.10 | 289 |
| 2b | OEt | —C$_{10}$H$_{21}$—$^n$ | C$_{12}$H$_{26}$ClO$_3$P | 0.79 (t, 3H, CH$_3$, J = 7H$_z$); 1.16 [m, 14H, —(CH$_2$)$_7$—]; 1.33 (t, 3H, OCH$_2$—CH$_3$, J = 7H$_z$); 1.65 (p, 2H, O—CH$_2$—CH$_2$, J = 7H$_z$); 4.10 (m, 2H, OCH$_2$—CH$_2$, J$_{H-H}$ = & & J$_{P-H}$ = 12H$_z$; 4.18 (m, 2H, OCH$_2$—CH$_3$, J$_{H-H}$ = 7 & J$_{P-H}$ = 12H$_z$) | 4.65 | 285 |
| 2c | OEt | —C$_{12}$H$_{25}$—$^n$ | C$_{14}$H$_{30}$ClO$_3$P | 0.81 (t, 3H, CH$_3$, J = 7H$_z$); 1.20 [m, 18H, —(CH$_2$)$_9$—]; | 4.59 | 313 |

TABLE 1-continued

Physical and spectroscopic data of substituted phosphates and phosphonates:

| Compd. No. 1 | R 2 | R' 3 | Mcl. formula 4 | $^1$H-NMR (ppm) 5 | $^{31}$P-NMR (ppm) 6 | Mass M/Z MH$^+$ 7 |
|---|---|---|---|---|---|---|
| | | | | 1.34 (t, 3H, OCH$_2$CH$_3$, J = 7H$_z$); 1.67 (p, 2H, OCH$_2$—CH$_2$—CH$_2$, J = 7H); 4.13 (m, 2H, OCH$_2$—CH$_2$, J$_{H\text{-}H}$ = 7 & J$_{P\text{-}H}$ = 12H$_z$); 4.21 (m, 2H, OCH$_2$—CH$_3$, J$_{H\text{-}H}$ = 7 & J$_{P\text{-}H}$ = 12H$_z$) | | |
| 2d | OEt | (CH$_2$)$_7$—CH=CH—(CH$_2$)$_2$—CH$_3$ (cis) | C$_{14}$H$_{28}$ClO$_3$P | 1.83 (t, 3H, CH$_3$, J = 7H$_z$); 1.24 [m, 10H, (CH$_2$)$_4$ & CH$_2$—CH$_3$]; 1.35 (t, 3H, OCH$_2$—CH$_3$, J = 7H$_z$); 1.68 (p, 2H, OCH$_2$—CH$_2$, J = 7H$_z$); 1.96 (m, 4H, CH$_2$—C=C—CH$_2$); 4.13 (m, 2H, OCH$_2$—CH$_2$, J$_{H\text{-}H}$ = 7 & J$_{P\text{-}H}$ = 12H$_z$); 4.21 (m, 2H, OCH$_2$—CH$_3$, J$_{H\text{-}H}$ = 7 & J$_{P\text{-}H}$ = 12H$_z$); 5.30 (m, 2H, CH=CH) | 4.75 | 311 |
| 2e | OEt | (CH$_2$)$_7$—CH=CH—(CH$_2$)$_2$—CH$_3$ (trans) | C$_{14}$H$_{28}$ClO$_3$P | 0.82 (t, 3H, CH$_3$, J = 7H$_z$); 1.24 [m, 10H, (CH$_2$)$_4$ & CH$_2$—CH$_3$]; 1.36 (t, 3H, OCH$_2$—CH$_3$, J = 7H$_z$); 1.67 (p, 2H, OCH$_2$—CH$_2$, J = 7H$_z$); 1.97 (m, 4H, CH$_2$—C=C—CH$_2$); 4.14 (m, 2H, OCH$_2$—CH$_2$, J$_{H\text{-}H}$ = 7 & J$_{P\text{-}H}$ = 12H$_z$); 4.22 (m, 2H, OCH$_2$—CH$_3$, J$_{H\text{-}H}$ = 7 & J$_{P\text{-}H}$ = 12H$_z$); 5.31 (m, 2H, CH=CH) | 4.68 | 311 |
| 2f | OEt | —C$_{14}$H$_{29}$$^{-n}$ | C$_{16}$H$_{34}$ClO$_3$P | 0.86 (t, 3H, CH$_3$, J = 7H$_z$); 1.26 [m 22H, —(CH$_2$)$_{11}$—]; 1.38 (t, 3H, OCH$_2$—CH$_3$, J = 7H$_z$); 1.73 (p, 2H, OCH$_2$—CH$_2$—CH$_2$, J = 7H$_z$); 4.18 (m, 2H, OCH$_2$—CH$_2$, J$_{H\text{-}H}$ = 7 & J$_{P\text{-}H}$ = 12H$_z$); 4.26 (m, 2H, OC$_2$—CH$_3$, J$_{H\text{-}H}$ = 7 & J$_{P\text{-}H}$ = 12H$_z$) | 4.60 | 341 |
| 2g | OPr-i | (CH$_2$)$_7$—CH=CH—(CH$_2$)$_2$—CH$_3$ | C$_{15}$H$_{30}$FO$_3$P | 0.81 (t, 3H, CH$_3$, J = 7H$_z$); 1.23 [m, 10H, (CH$_2$)$_4$ & CH2—CH$_3$]; 1.42 (d, 6H, 2 × CH$_3$, J = 7H$_z$); 1.64 (p, 2H, OCH$_2$—CH$_2$, J = 7H$_z$); 1.92 (m, 4H, CH$_2$—CH=CH—CH$_2$); 4.10 (m, 2H, OCH$_2$, J$_{H\text{-}H}$ = 7 & J$_{P\text{-}H}$ = 11H$_z$); 4.95 (m, 1H, OCH, J$_{H\text{-}H}$ = 7 & J$_{P\text{-}H}$ = 11H$_z$); 5.25 (m, 2H, CH=CH) | 3.70 | 309 |
| 2h | Me | C$_{12}$H$_{25}$$^{-n}$ | C$_{13}$H$_{28}$ClO$_2$P | 0.82 (t, 3H, CH$_3$, J = 7H$_z$); 1.17 [m, 18H, (CH$_2$)$_9$]; 1.64 (p, 2H, OCH$_2$—CH$_2$—CH$_2$, J = 7H$_z$); 1.90 (d, 3H, P—CH$_3$, J = 18H$_z$); 4.11 (m, 2H, OCH$_2$, J$_{H\text{-}H}$ = 7 & J$_{P\text{-}H}$ = 12H$_z$) | 40.31 | 283 |
| 2i | Me | (CH$_2$)$_7$—CH=CH—(CH$_2$)$_2$—CH$_3$ (cis) | C$_{13}$H$_{26}$ClO$_2$P | 0.83 (t, 3H, CH$_3$, J = 7H$_z$); 1.25 [m, 10H, —(CH$_2$) & CH$_2$—CH$_3$]; 1.66 (p, 2H, OCH$_2$—CH$_2$, J = 7H$_z$); 1.90 (d, 3H, P—CH$_3$, J = 18H$_z$); 1.94 (m, 4H, CH$_2$—C=C—CH$_2$); 4.10 (m, 2H, OCH$_2$, J$_{H\text{-}H}$ = 7 & J$_{P\text{-}H}$ = 12H$_z$); 5.27 (m, 2H, CH=CH) | 40.27 | 281 |
| 2j | O(CH$_2$)$_7$—CH=CH—(CH$_2$)$_2$—CH$_3$ (cis) | (CH$_2$)$_7$—CH=CH—(CH$_2$)$_2$—CH$_3$ (cis) | C$_{24}$H$_{46}$ClO$_3$P | 0.82 (t, 6H, 2 × CH$_2$, J = 7H$_z$); 1.25 [m, 20H, 2 × (CH$_2$)$_4$ & 2 × CH$_2$—CH$_3$]; 1.72 (p, 4H, 2 × OCH$_2$—CH$_2$, J = 7H$_z$); 1.94 (m, 8H, 2 × CH$_2$—C=C—CH$_2$); 4.25 (m, 4H, 2 × OCH$_2$, J$_{H\text{-}H}$ = 7 & J$_{P\text{-}H}$ = 11H$_z$); 5.26 (m, 4H, 2 × CH=CH) | 7.10 | 449 |
| 3a | OEt | C$_{12}$H$_{25}$$^{-n}$ | C$_{26}$H$_{55}$O$_4$P | 0.81 (t, 6H, CH$_3$, J = 7H$_z$); 1.18 [m, 36H, 2 × (CH$_2$)$_9$]; 1.26 (t, 3H, OCH$_2$—CH$_3$, J = 7H$_z$); 1.61 (p, 4H, 2 × OCH$_2$—CH$_2$, J = 7H$_z$); 3.95 (m, 4H, OCH$_2$—CH$_2$, J$_{H\text{-}H}$ = 7 & J$_{P\text{-}H}$ = 12H$_z$); 4.05 (m, 2H, OCH$_2$—CH$_3$, J$_{H\text{-}H}$ = 7 & J$_{P\text{-}H}$ = 12H$_z$) | 0.75 | 463 |
| 3b | Me | C$_{12}$H$_{25}$$^{-n}$ | C$_{25}$H$_{53}$O$_3$P | 0.81 (t, 6H, 2 × CH$_3$, J = 7H$_z$); 1.17 [m, 36H, 2 × (CH$_2$)$_9$]; 1.61 (p, 4H, 2 × OCH$_2$—CH$_2$—CH$_2$, J = | 30.76 | 433 |

TABLE 1-continued

Physical and spectroscopic data of substituted phosphates and phosphonates:

| Compd. No. 1 | R 2 | R' 3 | Mcl. formula 4 | $^1$H-NMR (ppm) 5 | $^{31}$P-NMR (ppm) 6 | Mass M/Z MH$^+$ 7 |
|---|---|---|---|---|---|---|
| | | | | 7H$_2$); 1.90 (d, 3H, P—C$\underline{H}_3$, J = 18H$_z$); 3.95 (m, 4H, 2 × OC$\underline{H}_2$, J$_{H-H}$ = 7 & J$_{P-H}$ = 12H$_z$); | | |
| 3c | Me | (CH$_2$)$_7$—CH=CH— (CH$_2$)$_2$—CH$_3$ (cis) | C$_{25}$H$_{49}$O$_3$P | 0.81 (t, 6H, 2 × C$\underline{H}_3$, J = 7H$_z$); 1.24 [m, 20H, 2 × (C$\underline{H}_2$)$_4$— & 2 × C$\underline{H}_2$—CH$_3$]; 1.64 (p, 4H, 2 × OCH$_2$—C$\underline{H}_2$, J = 7H$_z$); 1.88 (d, 3H, P—C$\underline{H}_3$, J = 18H$_z$); 1.95 (m, 8H, 2 × C$\underline{H}_2$—C=C—C$\underline{H}_2$); 3.95 (m, 4H, 2 × OC$\underline{H}_2$, J$_{H-H}$ = 7 & J$_{P-H}$ = 12H$_z$); 5.26 (m, 4H, 2 × C$\underline{H}$=C$\underline{H}$) | 30.53 | 429 |
| 4a | OMe | (CH$_2$)$_7$—CH=CH— (CH$_2$)$_2$—CH$_3$ | C$_{13}$H$_{26}$FO$_3$P | 0.82 (t, 3H, C$\underline{H}_3$, J = 7H$_z$); 1.25 [m, 10H, (C$\underline{H}_2$)$_4$ & C$\underline{H}_2$—CH$_3$]; 1.65 (p, 2H, OCH$_2$—C$\underline{H}_2$, J = 7H$_z$); 1.95 (m, 4H, C$\underline{H}_2$—CH=CH—C$\underline{H}_2$); 3.84 (d, 3H, OC$\underline{H}_3$, J = 12H$_z$); 4.12 (m, 2H, OC$\underline{H}_2$, J$_{H-H}$ = 7 & J$_{P-H}$ = 12H$_z$); 5.30 (m, 2H, C$\underline{H}$=C$\underline{H}$) | −7.8 (d) J$_{P-F}$ = 979H$_z$ | 281 |
| 4b | OEt | C$_{10}$H$_{21}$$^{-n}$ | C$_{12}$H$_{26}$FO$_3$P | 0.81 (t, 3H, C$\underline{H}_3$, J = 7H$_z$); 1.21 [m, 14H, (C$\underline{H}_2$)$_7$]; 1.34 (t, 3H, OCH$_2$—C$\underline{H}_3$, J = 7H$_z$); 1.65 (p, 2H, OCH$_2$—C$\underline{H}_2$, J = 7H$_z$); 4.12 (m, 2H, OC$\underline{H}_2$—CH$_2$, J$_{H-H}$ = 7 & J$_{P-H}$ = 12H$_z$); 4.19 (m, 2H, OC$\underline{H}_2$—CH$_3$, J$_{H-H}$ = 7 & J$_{P-H}$ = 12H$_z$) | −8.9 (d) J$_{P-F}$ = 979H$_z$ | 269 |
| 4c | OEt | C$_{12}$H$_{25}$$^{-n}$ | C$_{14}$H$_{30}$FO$_3$P | 0.81 (t, 3H, C$\underline{H}_3$, J = 7H$_z$); 1.20 [m, 18H, (C$\underline{H}_2$)$_9$—]; 1.33 (t, 3H, OCH$_2$—C$\underline{H}_3$, J = 7H$_z$); 1.65 (p, 2H, OCH$_2$—C$\underline{H}_2$, J = 7H$_z$); 4.10 (m, 2H, OC$\underline{H}_2$—CH$_2$, J$_{H-H}$ = 7 & J$_{P-H}$ = 12H$_z$); 4.18 (m, 2H, OC$\underline{H}_2$—CH$_3$, J$_{H-H}$ = 7 & J$_{P-H}$ = 12H$_z$) | −8.9 (d) J$_{P-F}$ = 979H$_z$ | 297 |
| 4d | OEt | (CH$_2$)$_7$—CH=CH— (CH$_2$)$_2$—CH$_3$ (cis) | C$_{14}$H$_{28}$FO$_3$P | 0.84 (t, 3H, C$\underline{H}_3$, J = 7H$_z$); 1.25 [m, 10H, (C$\underline{H}_2$)$_4$ & C$\underline{H}_2$—CH$_3$]; 1.34 (t, 3H, OCH$_2$—C$\underline{H}_3$, J = 7H$_z$); 1.67 (p, 2H, OCH$_2$—C$\underline{H}_2$—, J = 7H$_z$); 1.94 (m, 4H, C$\underline{H}_2$—C=C—C$\underline{H}_2$—); 4.12 (m, 2H, OC$\underline{H}_2$—CH$_2$, J$_{H-H}$ = 7 & J$_{P-H}$ = 12H$_z$); 4.20 (m, 2H, OC$\underline{H}_2$—CH$_3$, J$_{H-H}$ = & & J$_{P-H}$ = 12H$_z$); 5.29 (m, 2H, C$\underline{H}$=C$\underline{H}$) | −8.8 (d) J$_{P-F}$ = 979H$_z$ | 295 |
| 4e | OEt | (CH$_2$)$_7$—CH=CH— (CH$_2$)$_2$—CH$_3$ (trans) | C$_{14}$H$_{28}$FO$_3$P | 0.83 (t, 3H, C$\underline{H}_3$, J = 7H$_z$); 1.23 [m, 10H, (C$\underline{H}_2$)$_4$ & C$\underline{H}_2$—CH$_3$]; 1.32 (t, 3H, OCH$_2$—C$\underline{H}_3$, J = 7H$_z$); 1.65 (p, 2H, OCH$_2$—C$\underline{H}_2$, J = 7H$_z$); 1.94 (m, 4H, C$\underline{H}_2$—C=C—C$\underline{H}_2$); 4.11 (m, 2H, OC$\underline{H}_2$—CH$_2$, J$_{H-H}$ = 7 & J$_{P-H}$ = 12H$_z$); 4.19 (m, 2H, OC$\underline{H}_2$—CH$_3$, J$_{H-H}$ = 7 & J$_{P-H}$ = 12H$_z$); 5.31 (m, 2H, C$\underline{H}$=C$\underline{H}$) | −8.8 (d) J$_{P-F}$ = 979H$_z$ | 295 |
| 4f | OEt | —C$_{14}$H$_{29}$$^{-n}$ | C$_{16}$H$_{34}$FO$_3$P | 0.82 (t, 3H, C$\underline{H}_3$, J = 7H$_z$); 1.21 [m, 22H, (C$\underline{H}_2$)$_{11}$]; 1.34 (t, 3H, OCH$_2$—C$\underline{H}_3$, J = 7H$_z$); 1.65 (p, 2H, OCH$_2$—C$\underline{H}_2$, J = 7H$_z$); 4.11 (m, 2H, OC$\underline{H}_2$—CH$_2$, J$_{H-H}$ = 7 & J$_{P-H}$ = 12H$_z$); 4.18 (m, 2H, OC$\underline{H}_2$—CH$_3$, J$_{H-H}$ = 7 & J$_{P-H}$ = 12H$_z$) | −8.7 (d) J$_{P-F}$ = 979H$_z$ | 325 |
| 4g | OPr-i | (CH$_2$)$_7$—CH=CH— (CH$_2$)$_2$—CH$_3$ (cis) | C$_{15}$H$_{30}$FO$_3$P | 0.80 (t, 3H, C$\underline{H}_3$, J = 7H$_z$); 1.22 [m, 10H, (C$\underline{H}_2$)$_4$ & C$\underline{H}_2$—CH$_3$]; 1.32 (d, 6H, 2 × C$\underline{H}_3$, J = 7H$_z$); 1.64 (p, 2H, OCH$_2$—C$\underline{H}_2$, J = 7H$_z$); 1.94 (m, 4H, C$\underline{H}_2$—C=C—C$\underline{H}_2$); 4.08 (m, 2H, C$\underline{H}_2$, J$_{H-H}$ = 7 & J$_{P-H}$ = 12H$_z$); 4.72 (m, 1H, OC$\underline{H}$, J$_{H-H}$ = 7 & J$_{P-H}$ = 12H$_z$); 5.30 (m, 2H, C$\underline{H}$=C$\underline{H}$) | −9.1 (d) J$_{P-F}$ = 977 | 309 |
| 4h | Me | C$_{12}$H$_{25}$$^{-n}$ | C$_{13}$H$_{28}$FO$_2$P | 0.86 (t, 3H, C$\underline{H}_3$, J = 7H$_z$); 1.26 [m, 18H, (C$\underline{H}_2$)$_9$]; | 29.67 (d) | 267 |

TABLE 1-continued
Physical and spectroscopic data of substituted phosphates and phosphonates:

| Compd. No. 1 | R 2 | R' 3 | Mcl. formula 4 | $^1$H-NMR (ppm) 5 | $^{31}$P-NMR (ppm) 6 | Mass M/Z MH$^+$ 7 |
|---|---|---|---|---|---|---|
| | | | | 1.60 (dd, 3H, P—C$\underline{H}_3$, $J_{P-H}$ = 18 & $J_{F-H}$ = 6H$_z$); 1.65 (p, 2H, OCH$_2$—C$\underline{H}_2$, J = 7H$_z$); 4.10 (m, 2H, OC$\underline{H}_2$, $J_{H-H}$ = 7 & $J_{P-H}$ = 12H$_z$) | J = 1049H$_z$ | |
| 4i | Me | (CH$_2$)$_7$—CH=CH—(CH$_2$)$_2$—CH$_3$ (cis) | C$_{13}$H$_{26}$FO$_2$P | 0.82 (t, 3H, C$\underline{H}_3$, J = 7H$_z$); 1.25 [m, 10H, (C$\underline{H}_2$)$_4$ & C$\underline{H}_2$—CH$_3$]; 1.57 (dd, 3H, P—C$\underline{H}_3$, $J_{P-H}$ = 18 & $J_{F-H}$ = 6H$_z$); 1.64 (p, 2H, OCH$_2$—C$\underline{H}_2$, J = 7H$_z$); 1.94 (m, 4H, C$\underline{H}_2$—C=C—C$\underline{H}_2$); 4.12 (m, 2H, OC$\underline{H}_2$, $J_{H-H}$ = 7 & $J_{P-H}$ = 12H$_z$); 5.28 (m, 2H, C$\underline{H}$=C$\underline{H}$) | 29.61 (d) J = 1049H$_z$ | 265 |
| 4j | O(CH$_2$)$_7$—CH=CH—(CH$_2$)$_2$—CH$_3$ (cis) | (CH$_2$)$_7$—CH=CH—(CH$_2$)$_2$—CH$_3$ (cis) | C$_{24}$H$_{46}$FO$_3$P | 0.81 (t, 6H, 2 × C$\underline{H}_3$, J = 7H$_z$); 1.24 [m, 20H, 2 × (C$\underline{H}_2$)$_4$ & 2 × C$\underline{H}_2$—CH$_3$]; 1.62 (p, 4H, 2 × OCH$_2$—C$\underline{H}_2$, J = 7H$_z$); 1.90 (m, 8H, 2 × C$\underline{H}_2$—CH=CH—C$\underline{H}_2$); 4.06 (m, 4H, 2 × OC$\underline{H}_2$, $J_{H-H}$ = 7 & $J_{P-H}$ = 11H$_z$); 5.25 (m, 4H, 2 × C$\underline{H}$=C$\underline{H}$) | −8.6 (d) $J_{P-F}$ = 977H$_z$ | 433 |
| 4k | OEt | (CH$_2$)$_7$—CH=CH—(CH$_2$)$_2$—CH$_3$ (cis) | C$_{15}$H$_{28}$NO$_3$P | 0.83 (t, 3H, C$\underline{H}_3$, J = 7H$_z$); 1.23 [m, 10H, (C$\underline{H}_2$)$_4$ & C$\underline{H}_2$—CH$_3$]; 1.32 (t, 3H, OCH$_2$—C$\underline{H}_3$, J = 7H$_z$); 1.60 (m, 2H, OCH$_2$—C$\underline{H}_2$); 1.95 (m, 4H, C$\underline{H}_2$—C=C—C$\underline{H}_2$); 4.10 (m, 2H, OC$\underline{H}_2$—CH$_2$, $J_{H-H}$ = 7 & $J_{P-H}$ = 12H$_z$); 4.20 (m, 2H, OC$\underline{H}_2$—CH$_3$, $J_{H-H}$ = 7 & $J_{P-H}$ = 12H$_z$); 5.30 (m, 2H, C$\underline{H}$=C$\underline{H}$) | −12.39 | 302 |
| 4l | OEt | (CH$_2$)$_7$—CH=CH—(CH$_2$)$_2$—CH$_3$ (cis) | C$_{16}$H$_{33}$O$_3$PS | 0.86 (m, 6H, 2 × C$\underline{H}_3$); 1.25 [m, 10H, (C$\underline{H}_2$)$_4$ & C$\underline{H}_2$—CH$_3$]; 1.34 (t, 3H, OCH$_2$—C$\underline{H}_3$, J = 7H$_z$); 1.63 (m, 2H, OCH$_2$—C$\underline{H}_2$); 1.95 (m, 4H, C$\underline{H}_2$—C=C—C$\underline{H}_2$); 2.85 (m, 2H, SC$\underline{H}_2$); 4.09 (m, 2H, OC$\underline{H}_2$—CH$_2$); 4.15 (m, 2H, OC$\underline{H}_2$—CH$_3$); 5.29 (m, 2H, C$\underline{H}$=C$\underline{H}$) | 28.6 | 336 |
| 4m | NEt$_2$ | (CH$_2$)$_7$—CH=CH—(CH$_2$)$_2$—CH$_3$ (cis) | C$_{18}$H$_{38}$NO$_3$P | 0.84 (t, 3H, C$\underline{H}_3$, J = 7H$_z$); 1.0-1.14 (m, 9H, 3 × CH$_3$); 1.28 [m, 10H, (C$\underline{H}_2$)$_4$ & C$\underline{H}_2$—CH$_3$]; 1.34 (m, 6H, N(CH$_2$—C$\underline{H}_3$)$_2$]; 1.60 (p, 2H, OCH$_2$—C$\underline{H}_2$, J = 7H$_z$); 3.0 [m, 4H, N(CH$_2$)$_2$]; 3.90 (m, 2H, OC$\underline{H}_2$—CH$_2$—, $J_{H-H}$ = 7 & $J_{P-H}$ = 12H$_z$); 4.12 (m, 2H, OC$\underline{H}_2$—CH$_3$, $J_{H-H}$ = 7 & $J_{P-H}$ = 12H$_z$); 5.30 (m, 2H, C$\underline{H}$=C$\underline{H}$) | 16.4 | 348 |

TABLE 2
$^{19}$F Chemical shifts of fluoridates.

| Compound No. | $^{19}$F Chemical Shift ppm | $J_{P-F}$(H$_Z$) |
|---|---|---|
| 4a | 81.3 (d) | 977 |
| 4b | 81.3 (d) | 977 |
| 4c | 81.6 (d) | 977 |
| 4d | 81.9 (d) | 977 |
| 4e | 81.7 (d) | 977 |
| 4f | 81.6 (d) | 977 |
| 4g | 83.3 (d) | 977 |
| 4h | 103.5 (dq) | $J_{PF}$ = 1048 & $J_{FH}$ = 6H$_Z$ |
| 4i | 103.6 (dq) | $J_{PF}$ = 1048 & $J_{FH}$ = 6H$_Z$ |
| 4j | 81.0 (d) | 977 | d, doublet
dq, double quartet

TABLE 3
Responses of male *G. molesta* pre-exposed to female sex pheromone or fluoro analogs when tested in a wind tunnel bioassay and wing-fanning bioassay.
% of males flying upwind and locating pheromone source following pre-exposure to each μg loading of compound

| | 1000 | 100 | 10 | Control (no pre-exposure) | $X^2$ | df |
|---|---|---|---|---|---|---|
| 3c | + | + | + | | | |
| 4a | 60 | 50 | 60 | 56.2 | 0.28 | 3 |
| | +a | − | − | | | |
| 4b | 60 | 50 | 70 | 56.2 | 1.06 | 3 |
| | − | − | − | | | |
| 4c | 70 | 70 | 60 | 50.0 | 1.50 | 3 |
| | − | − | − | | | |
| 4d | 0 | 20 | 20 | 62.5 | 18.54* | 3 |
| | + | + | + | | | |
| 4e | 40 | 40 | 80 | 75.0 | 6.55 | 3 |
| | − | − | − | | | |
| 4f | 80 | 60 | 80 | 62.5 | 1.74 | 3 |

TABLE 3-continued

Responses of male *G. molesta* pre-exposed to female sex pheromone or fluoro analogs when tested in a wind tunnel bioassay and wing-fanning bioassay.

% of males flying upwind and locating pheromone source following pre-exposure to each μg loading of compound

| | 1000 | 100 | 10 | Control (no pre-exposure) | $X^2$ | df |
|---|---|---|---|---|---|---|
| 4g | −<br>+ | −<br>+ | −<br>+ | 87.5 | 3.31 | 3 |
| | 60 | 60 | 70 | | | |
| 4h | 70 | 80 | 40 | 75.0 | 4.59 | 3 |
| | − | − | − | | | |
| 4i | 40 | 70 | 50 | 68.7 | 2.94 | 3 |
| | + | + | + | | | |
| 4j | 0 | 0 | 10 | 68.7 | 23.50* | 3 |
| | + | + | + | | | |
| Z8-12:Ac | 0 | 0 | 0 | 62.5 | 23.86* | 3 |
| | + | + | + | | | |

*Controls significantly different from pre-exposed males in same row according to $x^2$ (p<0.001).
a) Ten moths tested for each concentration except for controls. in which 16 moths were tested.
b) wing-fanning bioassay:
+ males responded by vigorous wing fanning during exposure to analogs
− males failed to respond by vigorous wing fanning during exposure to analogs.

What is claimed is:

1. A compound of general formula I

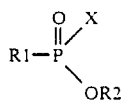

wherein
R1 represents —R3, —OR3 or —N(R3)$_2$, in which R3 is alkyl of 1 to 18 carbon atoms;
R2 represents alkyl of 1 to 18 carbon atoms; and
X represents halogen,
with the proviso that at least one of R2 and R3 is a sex pheromone alkyl chain selected from the group consisting of: cis—CH$_3$—(CH$_2$)$_5$—CH=CH—(CH$_2$)$_2$—; cis—CH$_3$—(CH$_2$)$_3$—CH=CH—(CH$_2$)$_4$; cis—CH$_3$—(CH$_2$)$_3$—CH=CH—(CH$_2$)$_6$—; cis—CH$_3$—(CH$_2$)$_2$—CH=CH—(CH$_2$)$_7$—; trans—CH$_3$—(CH$_2$)$_3$—CH=CH—(CH$_2$)$_6$—; cis—CH$_3$—(CH$_2$)$_5$—CH=CH—(CH$_2$)$_4$—; trans—CH$_3$—(CH$_2$)$_5$—CH=CH—(CH$_2$)$_4$—; trans—CH$_3$—(CH$_2$)$_2$—CH=CH—(CH$_2$)$_7$—; trans—CH$_3$—CH=CH—(CH$_2$)$_9$—; cis—CH$_3$—CH$_2$—CH=CH—(CH$_2$)$_8$—; trans—CH$_3$—CH$_2$—CH=CH—(CH$_2$)$_8$—; trans-8, trans-10-CH$_3$—CH=CH—CH=CH—(CH$_2$)$_7$—; cis—CH$_3$—(CH$_2$)$_7$—CH=CH—(CH$_2$)$_3$—; cis-4, trans-7-CH$_3$—(CH$_2$)$_4$—CH=CH—CH=CH—(CH$_2$)$_3$—; cis—CH$_3$—(CH$_2$)$_2$—CH=CH—(CH$_2$)$_9$—; trans-CH$_3$—(CH$_2$)$_4$—CH=CH—(CH$_2$)$_7$—; cis—CH$_3$—CH$_2$—CH=CH—(CH$_2$)$_{10}$—; trans-CH$_3$—CH$_2$—CH=CH—(CH$_2$)$_{10}$—; cis—CH$_3$—(CH$_2$)$_5$—CH=CH—(CH$_2$)$_6$—; cis—CH$_3$—(CH$_2$)$_3$—CH=CH—(CH$_2$)$_8$—; cis-9, trans-12-CH$_3$—CH=CH—CH$_2$—CH=CH—(CH$_2$)$_8$—; cis-9, trans-11-CH$_3$—CH$_2$—CH=CH—CH=CH—(CH$_2$)$_8$—; cis—CH$_3$—(CH$_2$)$_3$—CH=CH—(CH$_2$)$_{10}$—; cis—CH$_3$—(CH$_2$)$_5$—CH=CH—(CH$_2$)$_8$—; cis-7, cis-11-CH$_3$—(CH$_2$)$_3$—CH=CH—(CH$_2$)$_2$—CH=CH—(CH$_2$)$_6$—; cis-7, trans-11-CH$_3$—(CH$_2$)$_3$—CH=CH—(CH$_2$)$_2$—CH=CH—(CH$_2$)$_6$—; and cis-3, cis-13—CH$_3$—(CH$_2$)$_3$—CH=CH—(CH$_2$)$_8$—CH=CH—(CH$_2$)$_2$—.

2. A compound according to claim 1, wherein X is fluorine.

3. A compound according to claim 1, wherein R1 is —OCH$_2$CH$_3$, R2 is cis—(CH$_2$)$_7$—CH=CH—(CH$_2$)$_2$—CH$_3$ and X is F.

4. A compound according to claim 1, wherein R1 is O—cis—(CH$_2$)$_7$—CH=CH—(CH$_2$)$_2$—CH$_3$, R2 is cis—(CH$_2$)$_7$—CH=CH—(CH$_2$)$_2$—CH$_3$ and X is F.

5. A compound according to claim 1, wherein R1 is OCH(CH$_3$)$_2$, R2 is cis-(CH$_2$)$_7$—CH=CH—(CH$_2$)$_2$—CH$_3$ and X is F.

6. A compound according to claim 1, wherein R1 is CH$_3$, R2 is cis—(CH$_2$)$_7$—CH=CH—(CH$_2$)$_2$—CH$_3$ and X is F.

7. A method for disrupting the mating of an insect, comprising releasing into air in an area where mating of said insect is to be disrupted at least one compound of general formula I

wherein
R1 represents —R3, —OR3 or —N(R3)$_2$, in which R3 is alkyl of 1 to 18 carbon atoms;
R2 represents alkyl of 1 to 18 carbon atoms; and
X represents halogen,
with the proviso that at least one of R2 and R3 is a sex pheromone alkyl chain selected from the group consisting of: cis—CH$_3$—(CH$_2$)$_5$—CH=CH—(CH$_2$)$_2$—; cis—CH$_3$—(CH$_2$)$_3$—CH=CH—(CH$_2$)$_4$—; cis—CH$_3$—(CH$_2$)$_3$—CH=CH—(CH$_2$)$_6$—; cis—CH$_3$—(CH$_2$)$_2$—CH=CH—(CH$_2$)$_7$—; trans—CH$_3$—(CH$_2$)$_3$—CH=CH—(CH$_2$)$_6$—; cis—CH$_3$—(CH$_2$)$_5$—CH=CH—(CH$_2$)$_4$—; trans—CH$_3$—(CH$_2$)$_5$—CH=CH—(CH$_2$)$_4$—; trans—CH$_3$—(CH$_2$)$_2$—CH=CH—(CH$_2$)$_7$—; trans—CH$_3$—CH=CH—(CH$_2$)$_9$—; cis—CH$_3$—CH$_2$—CH=CH—(CH$_2$)$_8$—; trans—CH$_3$—CH$_2$—CH=CH—(CH$_2$)$_8$—; trans-8, trans-10-CH$_3$—CH=CH—CH=CH—(CH$_2$)$_7$—; cis—CH$_3$—(CH$_2$)$_7$—CH=CH—(CH$_2$)$_3$—; cis-4, trans-7-CH$_3$—(CH$_2$)$_4$—CH=CH—CH=CH—(CH$_2$)$_3$—; cis—CH$_3$—(CH$_2$)$_2$—CH=CH—(CH$_2$)$_9$—; trans-CH$_3$—(CH$_2$)$_4$—CH=CH—(CH$_2$)$_7$—; cis—CH$_3$—CH$_2$—CH=CH—(CH$_2$)$_{10}$—; trans-CH$_3$—CH$_2$—CH=CH—(CH$_2$)$_{10}$—; cis—CH$_3$—(CH$_2$)$_5$—CH=CH—(CH$_2$)$_6$—; cis—CH$_3$—(CH$_2$)$_3$—CH=CH—(CH$_2$)$_8$—; cis-9, trans-12-CH$_3$—CH=CH—CH$_2$—CH=CH—(CH$_2$)$_8$—; cis-9, trans-11-CH$_3$—CH$_2$—CH=CH—CH=CH—(CH$_2$)$_8$—; cis—CH$_3$—(CH$_2$)$_3$—CH=CH—(CH$_2$)$_{10}$—; cis—CH$_3$—(CH$_2$)$_5$—CH=CH—(CH$_2$)$_8$—; cis-7, cis-11-CH$_3$—(CH$_2$)$_3$—CH=CH—(CH$_2$)$_2$—CH=CH—(CH$_2$)$_6$—; cis-7, trans-11-CH$_3$—(CH$_2$)$_3$—CH=CH—(CH$_2$)$_2$—CH=CH—(CH$_2$)$_6$—; and cis-3, cis-13—CH$_3$—(CH$_2$)$_3$—CH=CH—(CH$_2$)$_8$—CH=CH—(CH$_2$)$_2$—,
in an amount effective to make it difficult for said insect to respond to or locate a mate through olfactory means.

8. A method according to claim 7, wherein a mixture of two or more compounds of general formula I is employed.

9. A method according to claim 7, wherein at least one compound of general formula I is employed in admixture with at least one sex pheromone component.

10. A method according to claim 7, wherein said at least one compound is administered in controlled release form.

11. A method according to claim 10, wherein said at least one compound is administered in a controlled-release matrix.

12. A method according to claim 11, wherein said controlled-release matrix is selected from the group consisting of microencapsulated beads, hollow fibers, porous tubes and laminated flakes.

13. A method according to claim 7, wherein said at least one compound is administered at an application rate of between about 0.1 gram to about 1000 grams per acre.

14. A method according to claim 13, wherein the application rate is between about 1 to about 100 grams per acre.

15. A method according to claim 7, wherein said at least one compound is administered from a first dispenser while simultaneously dispensing a naturally-occurring sex pheromone or sex pheromone mixture from a second, separate dispenser, thereby achieving an effective enhancement of field life of the naturally-occurring sex pheromone or sex pheromone mixture.

16. A method according to claim 7, wherein said insect is selected from the group consisting of Pyralidae, Tortricidae, Noctuidae, Gelechiidae, Sesiidae, Yponomeutidae, Lasiocampidae and Geometridae.

* * * * *

UNITED STATES PATENT AND TRADEMARK OFFICE
CERTIFICATE OF CORRECTION

PATENT NO. : 5,064,820

DATED : November 12, 1991

INVENTOR(S) : Fukuto, et al

It is certified that error appears in the above-identified patent and that said Letters Patent is hereby corrected as shown below:

In the Abstract, line 10, "which" should be -- with --.

Column 2, line 12, "mono" should read -- mono- --.

Column 7, line 1, ":" should read -- ; --.

Column 7 and 8, Table 1, in the entry for compd. 2b under heading $^1$H - NMR (ppm), in the fifth line thereof, "$J_{H-H}$ = &" should read -- $J_{H-H}$ = 7 & --; in the sixth line thereof, "12 Hz:" should read -- 12 Hz) --.

Columns 9 and 10, Table 1 - continued, in the entry for compd. 2d under heading $R^1$, in the first line thereof "CH$_2$)$_7$ - CH = CH-" should read -- (CH$_2$)$_7$ - CH = CH- --.

UNITED STATES PATENT AND TRADEMARK OFFICE
CERTIFICATE OF CORRECTION

PATENT NO. : 5,064,820

DATED : November 12, 1991

INVENTOR(S) : Fukuto, et al

It is certified that error appears in the above-identified patent and that said Letters Patent is hereby corrected as shown below:

Columns 9 and 10, Table 1 - continued, in the entry for compd. 2e under heading $R^1$, in the first line thereof "$CH_2)_7$ - CH = CH-" should read -- $(CH_2)_7$ - CH = CH- --.

Columns 11 and 12, Table 1 - continued, in the entry for compd. 3b, under heading $^1H$ - NMR (ppm), in the fourth line thereof "$J_{P-H}$ = 12Hz);" should read -- $J_{P-H}$ - 12 Hz) --.

Columns 11 and 12, Table 1 - continued, in the entry for compd. 4d, under the heading $^1H$ - NMR (ppm), in the eighth line thereof "$J_{H-H}$ = &" should read -- $J_{H-H}$ = 7 & --.

Signed and Sealed this

Thirtieth Day of March, 1993

*Attest:*

STEPHEN G. KUNIN

*Attesting Officer*     *Acting Commissioner of Patents and Trademarks*